United States Patent [19]

Zupanick et al.

[11] Patent Number: 4,687,335

[45] Date of Patent: Aug. 18, 1987

[54] TEMPERATURE COMPENSATION MEANS FOR A RADIOMETER

[75] Inventors: Joseph E. Zupanick; Clarence Braun, both of Richardson, Tex.

[73] Assignee: Atlantic Richfield Company, Los Angeles, Calif.

[21] Appl. No.: 806,961

[22] Filed: Dec. 9, 1985

[51] Int. Cl.⁴ .................................................. G01J 3/51
[52] U.S. Cl. .................................... 356/416; 356/417; 356/419
[58] Field of Search ..................... 356/414, 416–419; 250/352

[56] References Cited

U.S. PATENT DOCUMENTS

| | | | |
|---|---|---|---|
| 2,982,856 | 5/1961 | Camp | 250/352 |
| 3,598,994 | 8/1971 | Markle . | |
| 3,641,344 | 2/1972 | Markle . | |
| 3,769,516 | 10/1973 | Markle et al. . | |
| 3,864,037 | 2/1975 | Johnson | 356/418 |
| 4,227,802 | 10/1980 | Scholdstrom et al. | 356/381 |
| 4,233,513 | 11/1980 | Elder et al. | 356/418 |
| 4,336,459 | 6/1982 | Fay . | |
| 4,433,245 | 2/1984 | Poultney . | |

*Primary Examiner*—F. L. Evans
*Attorney, Agent, or Firm*—Drude Faulconer

[57] ABSTRACT

A radiometer for detecting and measuring components of luminescence and reflected light contained in a light beam from a target which included means for sensing the temperature of an optical filter in the radiometer and for adjusting the angular position of the mount which carries the filter in response to the sensed temperature to thereby retune the filter to its center frequency when changes in temperature occur. Longitudinal movement of an adjustment rod changes the angular position of the mount. A micrometer means manually moves the rod in one embodiment while a motor moves the rod in a second embodiment. The rod carries a means for sensing the longitudinal position of the rod (hence the rotational position of the mount) and generates a signal representative thereof. A means on the mount senses the temperature of the filter and generates a signal representative thereof. The temperature and position signals are compared by a processing circuitry which outputs an error signal if the position of the mount does not match a predetermined temperature signal. This error signal the (1) directly operates a control mechanism to move the adjustment rod which rotates the mount to a new angular position to retune the center frequency of the filter or (2) is fed to a visual indicator, which is brought back to a desired reference point by rotating the micrometer.

7 Claims, 16 Drawing Figures

TEMPERATURE COMPENSATION MEANS FOR A RADIOMETER

TECHNICAL FIELD

The present invention relates to a radiometer for detecting and measuring luminescense and reflectance of a unknown target material in the presence of ambient sunlight and more particularly relates to a means for tuning and maintaining the center frequency of an optical filter in a radiometer in response to changes in temperature of the filter.

BACKGROUND ART

Fraunhofer line discriminator systems are well known for sensing, measuring, and recording luminescence which is radiated from certain materials when stimulated by the sun. These systems operate on the known principle that sunlight contains identical Fraunhofer absorption lines before and after it is reflected from a material. In contrast, however, luminescence energy radiated from that material is broad band and contains no Fraunhofer absorption lines. Thus, luminescence produced by reflected sunlight can be sensed and measured by comparing the light level or intensity within a selected Fraunhofer absorption line to the light intensity in adjacent spectral regions (i.e. continuums) in which there is no Fraunhofer absorption line.

In their simpliest form, these Fraunhofer line discriminator systems employ a narrow passband filter tuned to pass a selected known Fraunhofer absorption line; a means to detect the intensity of reflected light within the selected Fraunhofer line; and means to detect the intensity of reflected light just outside the selected Fraunhofer line. The measured intensities are then applied to a well established, relationship to determine the intensity of the luminescence and reflectance of the measured material. For a more detailed description of these known Fraunhofer line discriminator systems and their operations, see U.S. Pats. Nos. 3,578,848; 3,598,994; 3,641,344; 3,769,516; and 4,433,245. While these known prior art systems provide measurements of luminescence, their design (especially that of large optical assemblies involved) has restricted their use to permanent installations, e.g. laboratories, or to large mobile units such as aircraft or satellites.

In co-pending U.S. application Ser. No. 746,050, filed June 18, 1985, and commonly assigned to the present assignee, a luminescence sensing and measuring apparatus (i.e. radiometer) is disclosed which utilizes a novel, simplified optical filter assembly which allows the apparatus to be of lightweight construction and highly portable thereby overcoming the use restrictions of the prior art systems. This lightweight optical filter assembly allows the apparatus to be hand carried into the field for measuring luminescence of target materials on site. To meet the desired lightweight requirement and still be functional over a wide range of Fraunhofer lines of possible interest, the elements of the primary optical filter assembly of the above-mentioned radiometer are mounted on a removable base element. This optical filter assembly is readily positioned into and removed from the radiometer during field operation. By having an individual optical filter assembly designed especially to sense the luminescence related to each of the specific Fraunhofer lines of interest, a particular assembly can be quickly interchanged into the radiometer to sense the luminescence about that particular Fraunhofer line.

More specifically, the lightweight optical filter assembly of the above-mentioned radiometer is comprised of three optical elements which are affixed in a defined relationship onto a base plate. The first element is a beamsplitter. The beamsplitter is positioned to lie in the line of sight with the light reflected from the material to be investigated when the optical filter assembly is in position in the radiometer. The combined visible reflected light and the light due to luminescense from the material is directed onto and is split by the beamsplitter. A large percentage of this light is reflected off the mirrored surfaces of the beamsplitter and continues through the second of the optical elements which, in turn, is a filter which is centered on the selected Fraunhofer line and which has a narrow passband (e.g. approximately 4 Angstroms). The light beam passing through the narrow band filter is focused by a lens system onto a first sensor which measures the intensity of said light beam. This measurement is representative of the intensity of light within the Fraunhofer line and is the "c" component of the known luminescence equation.

The remainder of the light passes through the beamsplitter and continues through the third optical element which is a filter centered on the selected Fraunhofer line and which has a broad passband (e.g. approximately 100 angstroms). The light beam passing through the wide band filter is focused by a lens system onto a second sensor which measures the intensity thereof. This measurement is representative of the intensity of the light in the continuums just outside the selected Fraunhofer line and is the "d" component of the luminescence equation.

In the radiometer described above, the adjustment or tuning of the narrow passband filter to its center frequency (i.e. selected Fraunhofer line frequency) and maintaining same during operation is an important factor in obtaining highly accurate readings of the light passing through the filter. This is due to the fact that the quantity being measured is relatively small in relation to the other values in the luminescense equation. The narrow passband filter is positioned at a shallow angle with respect to the light beam passing therethrough so that the light beam is slightly off normal with respect to the surface of the filter. The center frequency can be finely tuned as the temperature of the filter changes and maintained at its desired value by increasing or decreasing this shallow angle by moving adjustment rod by rotating a micrometer which extends through the front panel of the radiometer. The rod is in contact with a pivotable, spring biased mount on the optical filter assembly which carries the narrow passband filter. As the rod moves inward, the shallow angle is increased. Outward movement of the rod allows the spring biased mount to move in an opposite direction to decrease the shallow angle.

The narrow passband filter is comprised of optical quality glass which has such a low temperature expansion co-efficient that it would at first appear that normal changes in the ambient temperature during operation would have a negligible effect on the filter and hence, on the tuning of its center frequency. Nonetheless, this small temperature expansion coefficient does exist and it has been known that this coefficient causes changes in the tuning or alignment of the center frequency of the narrow passband filter in response to temperature changes, which, in turn, results in an error in the light readings being sensed through this filter. Compensation for this error, albeit small, is important since the overall accuracy of the measurements taken by the radiometer depends on accurately measuring small differences in otherwise relatively large numbers.

When this error associated with temperature was first dealt with, it was corrected by simply taking frequent temperature readings of the radiometer during use and consulting a calibration chart (previously prepared in the laboratory for the specific narrow passband filter in tune for the measured temperature). While effective, this procedure significantly slows field operations since the filter should be retuned with temperature changes as small as 0.1 degree centigrade which significantly affects the precision of the readings.

It can be seen from the above, it is highly desireable to provide a means for continuously sensing any temperature changes of the narrow passband filter and for quickly compensating therefor by fine tuning the narrow passband filter as the need arises without continuously consulting a chart or the like.

DISCLOSURE OF THE INVENTION

The present invention provides a radiometer for detecting components of luminescense and reflected light contained in a light beam from a target which included means for sensing the temperature of an optical filter in the radiometer and for adjusting the rotational position of said filter in response to the sensed temperature to thereby retune the filter to its center frequency when changes in temperature occur.

More specifically, the radiometer of the present invention comprises a housing having a aperture through which a light beam from the target enters the radiometer. An optical filter assembly is removably mounted in the housing and is designed to sense certain values of luminescense and reflectance related to a particular Fraunhofer absorption line which is present in the reflected light contained in the light beam from the target. As will be understood, a particular optical assembly is removed and replaced with a different particular Fraunhofer line optical assembly when a measurement is to be made of unknown material from which light is reflected having the different particular Fraunhofer line.

The optical filter assembly of the present invention includes a mount pivotably mounted on a base plate in which a passband filter is mounted so that it will be positioned directly in the path of at least a fraction of the light beam when in its operable position. The optical filter has a center frequency substantially equal to the particular Fraunhofer line contained in the light beam. The filter is tunable to its center frequency by rotating the mount to selected positions about its axis on the base plate.

An adjustment rod in the housing has one end in contact with the mount whereby longitudinal movement of the rod changes the angular position of the mount. A micrometer means manually moves the rod in one embodiment while a control mechanism moves the rod in a second embodiment. The rod carries a means for sensing the longitudinal position of the rod (hence the angular position of the mount) and generates a signal representative thereof.

A means is mounted on the mount for sensing the temperature of the optical filter and generates a signal representative thereof. The temperature and position signals are supplied to processing circuitry which compares the signals and outputs an error signal if the position of the mount does not match a predetermined temperature signal. This error signal then directly operates the control mechanism in the one embodiment to move the adjustment rod which rotates the mount to a new position to retune the center frequency of the optical filter to its desired Fraunhofer line frequency. In the manual embodiment, the error signal is fed to a visual indicator, e.g. zero center voltage meter, which is brought back to a desired reference point by rotating the micrometer to move the adjustment rod.

By constantly sensing the temperature of the optical filter, the filter can be automatically and/or manually retuned to its center frequency as the need arises without requiring external charts or special tools and without any substantial delay in operations. Also, the ability to constantly fine tune the narrow passband filter of the radiometer, the accuracy of the readings made thereby is greatly increased.

BRIEF DESCRIPTION OF THE DRAWINGS

The actual construction, operation, and apparent advantages of the present invention will be better understood by referring to the drawings in which like numerals identify like parts and in which.

BEST MODE FOR CARRYING OUT THE INVENTION

Figure 1A:
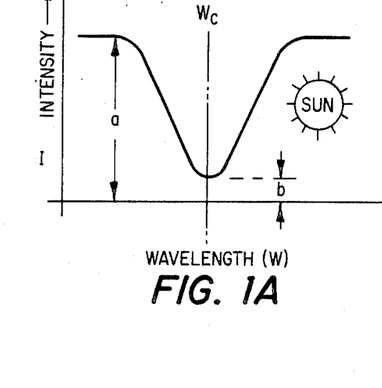
FIG. 1A and 1B are idealized graphic illustrations of the relationship of a Fraunhofer line present in the sun and the narrow "C" channel characteristics and their relationships which are used to calculate luminescense.
Figure 1B:
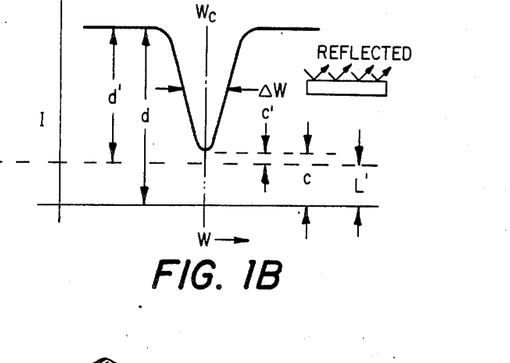

In order to better appreciate the present invention, a brief discussion of known luminescense phenomena will be set forth before the details of the invention are described. FIG. 1A is a idealized graphical illustration of light intensity (I) of sunlight over a portion of the spectrum which includes a particular Fraunhofer line $W_c$ over an average bandwidth $\Delta W$. While a particular Fraunhofer line is usually referred to as a single number, e.g. 5890 angstroms, this number, in fact, represents the center wave length of the Fraunhofer line which actually encompasses a narrow bandwidth. FIG. 1B is a graphical representation of light intensity (I) of reflected sunlight plus any luminescense (L) from a target (e.g. a material under investigation). In FIGS. 1A and 1B:

- a = light intensity in the continuum adjacent to a selected Fraunhofer line ($W_c$) for a sunlight sky scene;
- b = light intensity in a narrow spectral band centered at the Fraunhofer line ($W_c$) for said sky scene;
- c = light intensity in a narrow spectral band centered at the Fraunhofer line ($W_c$) which emanates from the material under investigation (target); and
- d = light intensity in the continuum adjacent the Fraunhofer line ($W_c$) which emanates from the target.

The following relationships can be established referring to FIGS. 1A and 1B:

$d'/a = c'/b = R$ (Reflection Coefficient)
$L'/a = L$ (Luminescense Coefficient)
$c = c' + L'$ and $d = d' + L'$ Then:

$$c = Rb + La$$

$$d = Ra + La$$

Solving these two equations simultaneously gives:

$$R = [(d-c)/(a-b)] \text{ and}$$

$$L = [d/a] - [(d-c)/(a-b)] = [d/a] - R$$

It has been found, however, that the ratio b/a is a very convenient system parameter and can be determined without direct measurement of the values of a and b. However, a measurement has to made to represent the scaling factor "a" in the above relationship. This measurement is made using a fairly broad band instrument looking vertically into the sky scene. The expression for luminescense (L) can be simplified as follows:

$$L = [d/a][((c/d)-n)/(1-n)] \text{ or}$$

$$L = \frac{1}{a(1-n)} [c - nd]$$

wherein:

$$n = b/a$$

Figure 2:
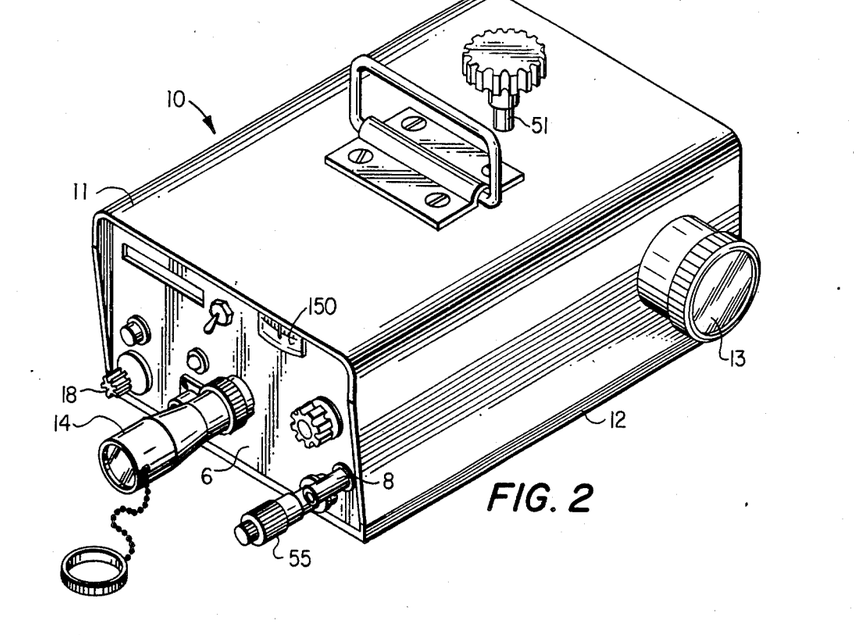
FIG. 2 is a perspective view of a typical external configuration of a radiometer in accordance with the present invention.

The present invention provides a lightweight and highly portable apparatus for actually measuring the c and d intensities of light emanating from a target material which are then used in the above expression to arrive at the luminescense component emanating from the target material. More particularly, FIG. 2 illustrates a typical external configuration of luminescense sensing means 10, hereinafter called a "radiometer". Radiometer 10 is comprised of a housing 11 having a box-like case which is removably mounted on a base 12 and front panel 6.

Housing 11 has a target aperture 13 through the side thereof. A viewfinder eyepiece 14 extends through front panel 6 of the radiometer 10 for a purpose that will become obvious below. Various other switches and controls are positioned through and on front panel 6 and top of housing 11 and will be discussed at the appropriate times during the following description.

Figures 3, 5:
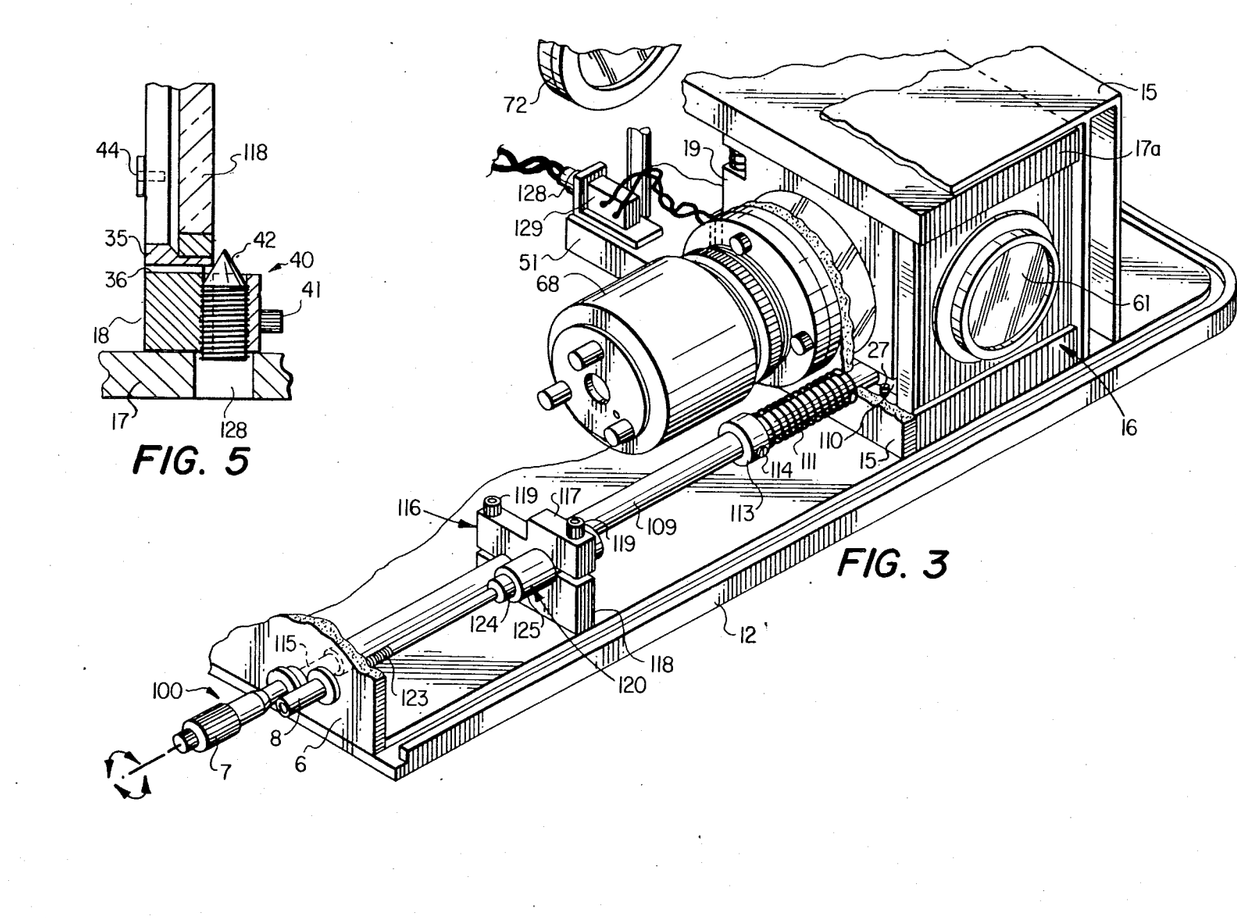
FIG. 3 is a cutway view of a portion of the internal structure of the radiometer of FIG. 1.
FIG. 5 is a sectional view taken along line 5—5 of FIG. 4.
Figures 4, 6:
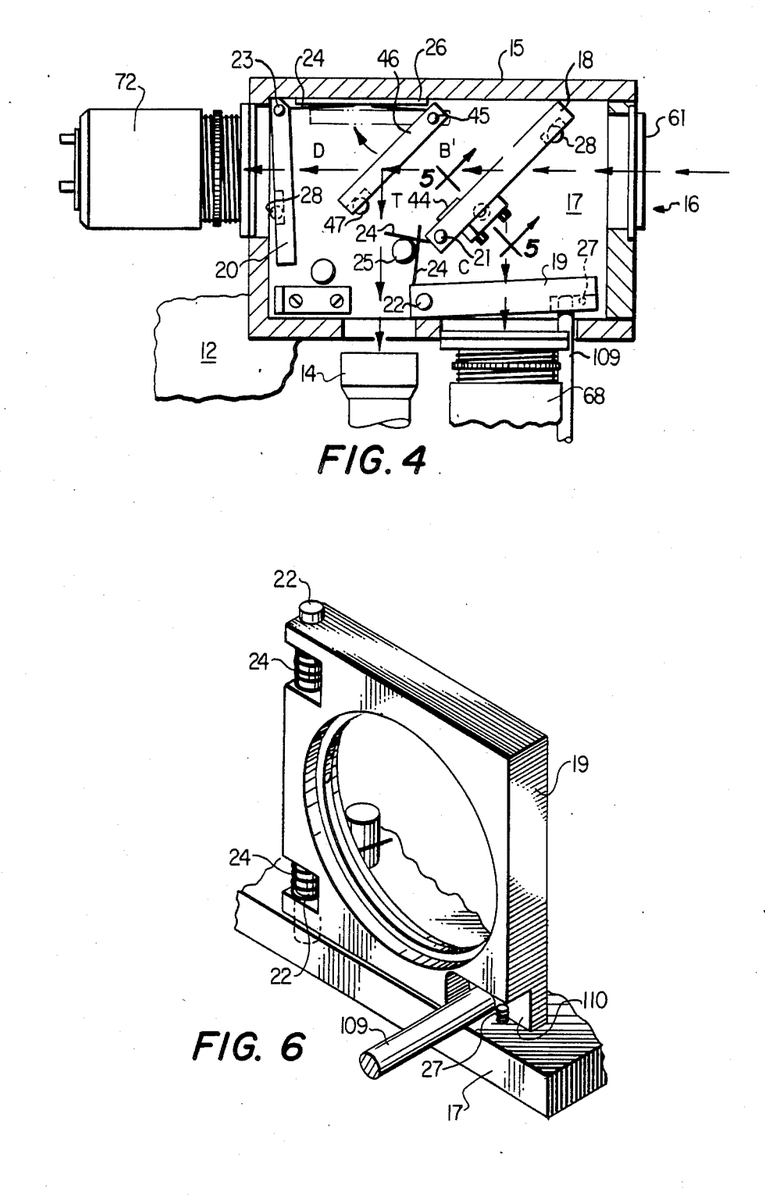
FIG. 4 is a top view of the optical assembly of the present invention in place in the radiometer.
FIG. 6 is a perspective view of the mount for the narrowband filter of the optical assembly of FIG. 4.

Referring now to FIGS. 3 and 4, a compartment 15 (shown partly broken away) is provided on base 12 into which optical filter assembly 16 is removably positioned. As seen in FIGS. 4–7, optical filter assembly 16 is comprised of a base plate 17 having a beamsplitter mount 18 and two filter element mounts 19 and 20, all pivotably mounted between base plate 17 and upper plate 17a (FIG. 3) by vertical pivot pins 21, 22 and 23, respectively, for rotational movement about a vertical axis. Torsional springs 24 encompass respective pins 21, 22 and 23 and have ends that bear against stops (e.g. stub posts 25, plate 26 respectively) to bias said mounts in a first rotational direction. Mount 19 (FIG. 7) is braced against stop 27 while mounts 18 and 20 are braced against adjustable stops 28. Adjustable stops 28 are of the same basic construction and each is comprised of a screw which is threaded upward through plate 17 and which has a conical upper end or tip (not shown) which cooperates with a complementary tapered surface (not shown) on the respective mount 18, 20. It will be understood that the conical tip will bear against the surface on the mount as the screw is threaded upward to cam (i.e. rotate) its respective mount against the bias of springs 24 to angularly align said mount about its respective vertical axis.

While filter mounts 19 and 20 are similar in construction, due to the function to be performed by the beamsplitter, a more universal adjustment is desired of beamsplitter mount 18. As seen in FIGS. 5 and 6, a retainer ring 35 is pivotably mounted within a horizontal opening 36 through mount 18 by pins 37 for rotational movement about a horizontal axis. Adjustment means 40 is mounted on mount 18 by screws 41 or the like and has a conically-tipped screw 42 threaded therethrough. The conical surface of screw 42 cooperates with the lower edge of ring 35 to rotate same about pins 37 and against the bias of a leaf spring 44 or the like (FIG. 4) which, in turn, is affixed to mount 18 on the side opposite adjustment means 40.

Also pivotably mounted on plate 17 by pivot pins 45 is mirror mount 46. Springs 24 which engage plate 26 normally biases mount 46 out against adjustable stop 47 which is of the same construction as that of stops 28 described above. Mirror mount 46 is mounted to be rotated about pins 45 into the optical path of a light beam passing through optical assembly 16 as will be explained below. Mount 46 is rotated by a shaft 51 which extends through upper plate 17a and through housing 11 (FIG. 2) between its retracted or stowed position (dotted lines in FIG. 4) and its operable position against stop 47 (FIG. 4). The purpose for moving mirror mount 46 between its two positions will become obvious from the discussion of operation set forth below.

The heads of all the screws of the adjustable means 28, 28a and 47 are accessible from the underside of housing 11 through openings 128 (only one shown in FIG. 5) in base plate 17 of optical assembly 16 which align with complementary openings (not shown) in base 12 when optical assembly 6 is in an operable position within housing 11. A removable cover plate (not shown) is positioned over the complimentary openings when not in use to block entry of any extraneous light into the housing. A tool, e.g. allen-head wrench, can be inserted through the aligned openings to rotate a particular screw of an adjustment means to fine-tune the beamsplitter mount 18 (both vertically and horizontally), filter mount 20, and mirror mount 46 to accurately align the components.

It will be understood that optical assembly 16 as described above is easily placed and removed from compartment 15 on base 12. By being able to replace the optical filter assembly 16 within radiometer 10, an individual assembly 16 can be designed and constructed for each individual Fraunhofer line of interest so that materials having luminescense at different Fraunhofer lines can be examined in the field by merely exchanging the appropriate optical filter assemblies 16.

Now that the mechanical details of optical filter assembly 16 have been described, the optical details of radiometer 10 will now be set forth. This may be best understood by referring to FIG. 7 which schematically illustrates the pathes that the various light beams take through radiometer 10. First, radiometer 10 is sighted onto target 60 (e.g. material from which luminescense is to be measured). This is done by rotating shaft 51 (FIGS. 1 and 6) to move a reflecting mirror 146 carried by mirror mount 46 to the operable position shown in FIG. 8. Light from target 60 will pass through beamsplitter 118 carried by retainer ring 35 in mount 18 and will be reflected by mirror 146 into eyepiece 14. Once radiometer 10 is properly sighted on the target, mirror 146 is retracted to its stowed position (dotted lines in FIG. 7).

Figures 8, 9, 10, 11:
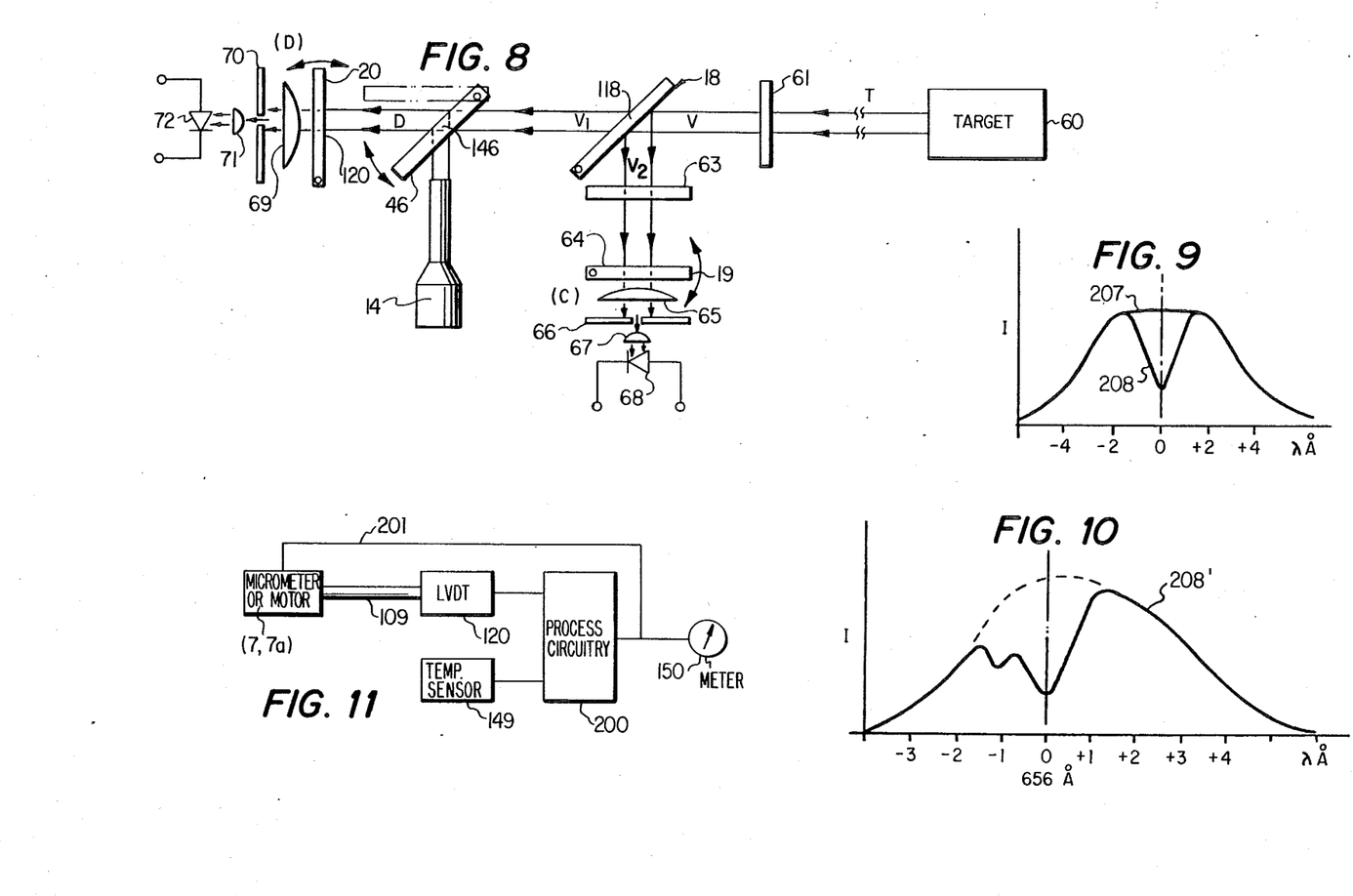
FIG. 8 is a schematical view of the optical filter assembly of the present invention of the present invention and the respective light paths therethrough.
FIG. 9 is a spectral diagram illustrating an idealized curve of light energy of a filter when centered about its center frequency which is equal to a particular Fraunhofer line.
FIG. 10 is a spectral diagram of the filter of FIG. 9 illustrating the effects caused by slight mistuning of its center frequency caused by a change in temperature of the filter.
FIG. 11 is a schematic diagram of the temperature sensing and compensating circuitry of the present invention.

Light T from target 60 (both reflected light and light due to luminiscense) enters radiometer 10 through target aperture 13 and passes through a broad bandwidth filter 61 (e.g. 3000-8000 angstroms) to produce a light beam V which is limited to the visible and spectrum light T from the target. Light beam V then impinges upon beamsplitter 118.

A first fraction $V_1$ of light beam V passes directly through beamsplitter 118 and then passes through filter 120 which is carried by filter mount 20. Filter 120 has a broad passband (full width half maximum) of approximately 100 Angstroms centered on the selected Fraunhofer line of interest. The light beam D from filter 120 next passes through lens 69, field stop 70, condensing lens 71, and onto photodiode 72, which measures the intensity of D. This measurement is representative to the "d" component or factor needed to calulate the luminescense and reflectance from target 60.

A second fraction $V_2$ of light beam V is reflected and redirected from the angular positioned beamsplitter 118. The second fraction $V_2$ passes through blocking filter 63 which has a nominal bandwidth (full width half maximum) of approximately 100 Angstroms centered on the selected Fraunhofer line. Filter 63 serves to eliminate the unwanted multiple transmission bands which would otherwise increase the apparent energy (i.e. intensity) reading at the Fraunhofer line frequency.

Light passing through filter 63 continues through narrow passband filter 64. Filter 64 is a tuneable filter having a narrow passband frequency of approximately 4 angstroms (i.e. full width, half maximum bandwidth) which is centered on the selected Fraunhofer line. It should be understood that both filters 63 and 64 can both be mounted in mount 19 as shown in FIG. 6 or their optical functions can be combined into a single unit such as filter units fabricated by Barr Associates of Massachussetts.

The light beam C passing through narrow passband filter 64 next passes through a lens 65, a field stop 66, condensing lens 67, and onto photodiode 68 which measures the intensity of C which represents the "c" component of the luminescense and reflectance equations set forth above.

Photodiodes 68 and 72 are blue-enhanced photovoltaic devices, e.g. model SD-200-12-12-241, distributed by Silicon Detector Corporation, which produce signals representative of the measured intensities and which can be stored or supplied directly to a processing means (not shown) for determining the luminescense and reflectance emanating from the target 60.

For a further description of the construction details and the operation of radiometer 10 as described to this point, see U.S. Pat. Application Ser. No. 746,050, filed June 18, 1985, and incorporated herein by reference.

Due to the very narrow passband of filter 64, one of the more critical adjustments in radiometer 10 is that of the angular position of filter mount 19, which controls the center frequency of filter 64 carried thereby. The effects of the angular position of mount 19, hence filter 64, on the readings at sensor 68 are seen by comparing the graphs of FIGS. 9 and 10. In FIG. 9, curve 207 represents the composite passband of blocking filter 63 and narrow passband filter 64, both of which are mounted in mount 19. Curve 208 represents the light beam $C^1$ which is concentrated by lens 65 (FIG. 8) and limited by stop 66 onto sensor 68 with the light energy stimulatingsensor 68 being that represented by the area under curve 208.

Filter 64 is comprised of optical quality glass. While its coefficient of expansion is small, it nevertheless has been found that it can adversely affect the readings taken at sensor 68. This results from the fact that radiometer 10 must accurately measure small differences in otherwise relatively large values. The effect of a slight temperature change in the narrow passband filter 64 on the light energy impinging on sensor 68 may best be understood by referring to FIG. 10 which is of the same scale as FIG. 9.

In FIG. 10, curve 208' represents light beam C' which has been detuned from the center line of the Faunhofer line by one angstrom as a result of temperature drift. It is apparent that the total areas under curves 208 (FIG. 9) and 208' (FIG. 10) are siginificantly different and which affect the accuracy of the measurement.

To compensate for changes in ambient temperature during operation, adjustment means are provided in radiometer 10 for sensing any changes in temperature in filter 64 and for angularly adjusting mount 19 to tune and maintaining the center frequency of filter 64 to the Fraunhofer line.

In a manual embodiment, the angular positioning of mount 19 is accomplished by adjustment means 100 which is comprised of a micrometer 7 which, in turn, is mounted on and through front panel 6. Adjustment rod 109 extends from the longitudinal translatable end 115 of micrometer 7 into abutment with recess 110 on mount 19 (FIGS. 3 and 6). Spring 111 is mounted on rod 109 and abuts at one end against compartment 15 and at its other end against a stop ring 113 which, in turn, is secured to rod 109 by set screw 114. Spring 111 will normally bias rod 109 into engagement with the end 115 of micrometer 7. It can be seen that by rotating micrometer 7, rod 109 will be moved inwardly or outwardly very precisely to rotate mount 19 about its pivot pins 22 to accurately angularly align mount 19.

A tranducer mount 116 comprising an upper section 117 and a lower section 118 is fixedly mounted on rod 109 by screw 119 or the like. Mount 116 carries the body 125 of a linear voltage/displacement transducer (LVDT) 120, which is positioned parallel to rod 109. It will be understood that mount 116 and hence body 125 will be moved by movement of rod 109 and the linear position of body 125 is directly related to the linear position of rod 109 and hence, the angular position of mount 19.

Slug 124 is slidably positioned in body 125 of LVDT 120 and has a rod 8 attached thereto which, in turn, threadedly extends through panel 6. As will be understood, LVDT 120 generates a signal representative of the precise axial or linear position of slug 124 in body 125. Therefore, the mutual axial position of the LVDT slug 124 with respect to the LVDT body 125 is determined by both: (1) the axial position of rod 8 and (2) the axial position of the rod 109 (which is analogous to the angular position of the narrow passband filter 34) as adjusted by the micrometer head 7. As will be discussed in detail below, this arrangement is advantageously employed to conveniently effect very precise temperature compensation to the passband center frequency of the narrow passband filter 64 carried by the optical mount 19.

Figure 7:
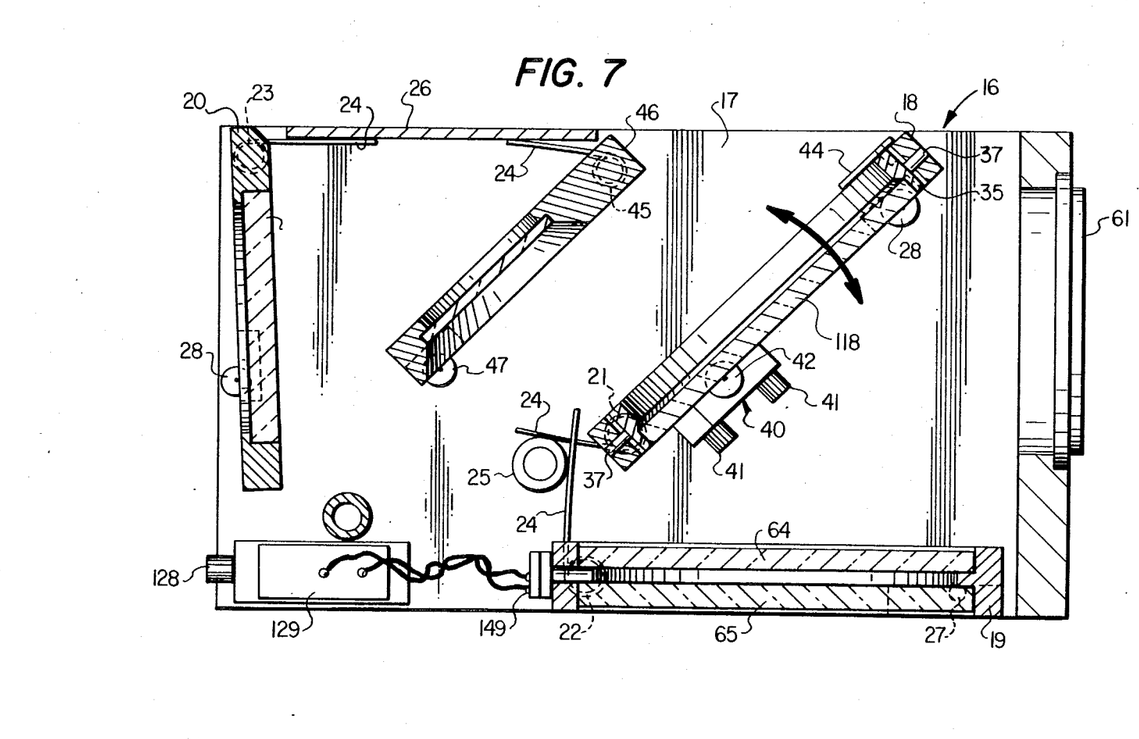
FIG. 7 is a view similar to FIG. 4 having additional details of the temperature sensing elements.

Referring to FIGS. 3 and 7, temperature sensor 149 is mounted on mount 19 at the edge of the sealed space between filters 63, 64 to continuously sense the temperature of the filter 64. Sensor 149 is preferably of the type such as an Analog Devices type AD590K used with precision film resistors with its output characteristic being linear with temperature in accordance with an equation of operation, e.g. 1 $\mu$amp/°K. Sensor 149 is connected by leads 149a to a jack 129 on optical filter assembly 16 which, in turn, has a plug 128 which is adapted to releasably couple sensor 149 to the processing circuitry 200 (FIGS. 11 and 12) within radiometer 10.

Figure 13:
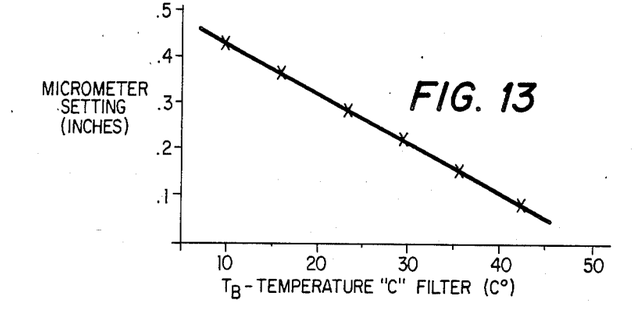
FIG. 13 is a graphic representation of a typical calibration curve for compensating for temperature change.

Basically, processing circuitry 200 receives the output signal from temperature sensor 149 and compares it to the output signal from LVDT 120. For a particular filter 64, various positions of slug 124 of LVDT 120 have been correlated with respective temperatures at which the center line of filter 64 will be properly tuned (e.g. see FIG. 13 for a typical calibration chart for a particular filter 64). When the signal from sensor 149 corresponds to the proper position signal from LVDT 120, the signals match and there is no output signal from circuity 200. However, if the temperature of filter 64 changes, the signal from sensor 149 will change and will no longer match the signal from LDVT. This results in the output of an "error" signal from circuitry 200 which is fed to a null meter 150 or equivalent.

By rotating micrometer 7, rod 109 simultaneously adjusts mount 19 and slug 124 to a position where LDVT is now outputting the required signal to match that now being received from temperature sensor 149. This centers null meter 150, telling the operator that filter 64 is properly retuned.

Figure 12:
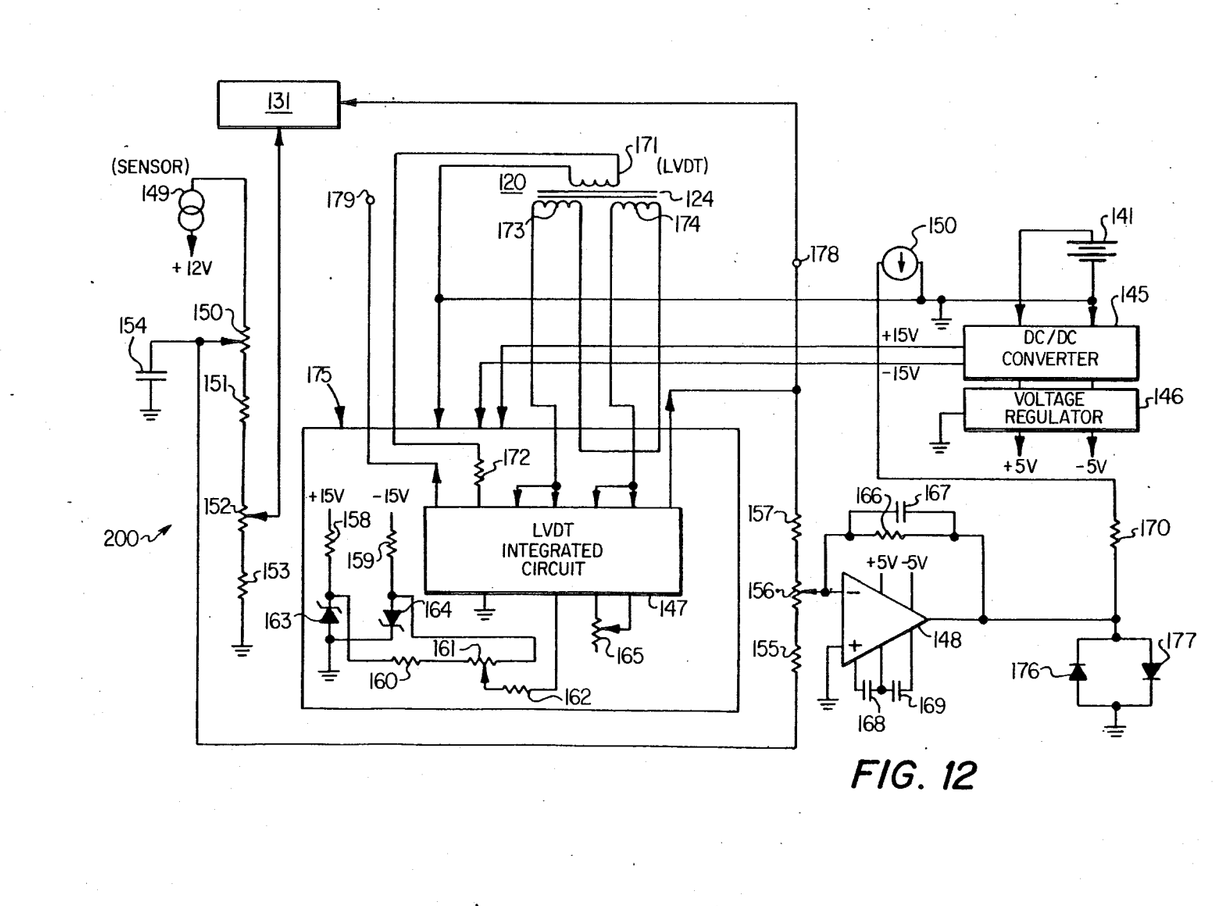
FIG. 12 is a detailed schematic of the circuitry of FIG. 11.

For a more detailed description of circuitry 200, reference is now made to FIG. 12 wherein primary winding 171 of the LVDT 120 has one end connected to ground and the other end connected, through isolation resistor 172, to a terminal of the integrated circuit 147 which supplies an a-c excitation signal of predetermined frequency and amplitude to the primary winding 171. Secondary windings 173 and 174 of the LVDT 120 are series connected in a polarity which causes their fields to oppose one another. The remaining terminal of each secondary winding 173 and 174 is connected to an input of the integrated circuit 147 which senses the induced amplitude of the signals appearing in each secondary winding 173, 174 and develops a d-c output signal indicative of the position of the slug 124 in the body 125 of the LVDT 120. Intergrated circuit 147 is of the type commercially available as part of an SMS/GPM/LDVT signal conditioning module 175, distributed by Schaevitz Engineering of Camden, N.J., which also distribute an LVDT (e.g. model 100 MHR) which can be used as LVDT 120.

A circuit for providing an adjustable negative reference voltage to integrated circuit 147 includes resistor 158, resistor 159, resistor 160, potentiometer 161, resistor 162, zener diode 163 and zener diode 164. Resistor 158 has one end connected to +15-volts d-c and its other end connected to the cathode of zener diode 163. Resistor 159 is connected at one end to −15-volts d-c and its other end connected to the anode of zener diode 164. The anode of zener diode 163 and the cathode of zener diode 164 are connected together and to ground potential. The resistor 160 and potentiometer 161 are disposed in series across voltage stabilized points defined by the cathode of zener diode 163 and the anode of zener diode 164. The tap of potentiometer 161 is connected to one end of isolation resistor 162 which has its other end connected to the reference input of integrated circuit 147. Zener diodes 163 and 164, are each rated at a specific value, e.g. 6.2 volts. Resistor 160 and potentiometer 161 have the same value, e.g. 10K ohms. Thus, since integrated circuit 147 draws negligible current from the voltage reference circuit, tap of potentiometer 161 may be adjusted to provide a reference voltage (e.g. falling between 0 and −6.2 volts d-c) to integrated circuit 147. The potentiometer 161 is the "offset" adjustment for the LVDT integrated circuitry at micrometer midrange at 25° C. and is adjusted to give zero error signal output from integrated circuit 147 when there is no error at those conditions. Another adjustment is provided by potentiometer 165 with which the gain of the integrated circuit 147 may be set for scaling the slope of the calibration curve in FIG. 13.

Integrated circuit 147 thus provides a negative signal output which is directly indicative of the precise longitudinal position of LVDT slug 124 with respect to LVDT body 125 and this signal is inputted into summing amplifier 148, e.g. Intersil ICL 7650, where it is compared with a signal from temperature sensor 149.

The temperature sensor 149 is connected in a series circuit disposed between +12 volts d-c and ground potential. The series circuit comprises the temperature sensor 149, a potentiometer 150, a resistor 151, a potentiometer 152, and a resistor 153. The tap of potentiometer 150, stabilized against rapid voltage changes by capacitor 154, is connected to one end of another series circuit comprising resistor 155, potentiometer 156, and resistor 157 which has its other end connected to one output terminal of integrated circuit 147 and also to test point 178 which defines an analog input to multiplexer and programmable gain amplifier 131. The tap of potentiometer 152 is connected to the multiplexer and programmable gain amplifier unit 131 to provide another analog input (a preferred analog voltage range having been obtained with the resistive voltage dividing circuitry) which is representative of the instantaneous temperature of the sensor 149.

The tap of potentiometer 156 is connected to the negative input of summing amplifier 148, and the positive input to summing amplifier 148 is connected to ground potential. A feedback network comprising resistor 166 and parallel capacitor 167 serves to set the gain of summing amplifier 148, in accordance with conventional practice, to match the range of meter 150 to the signal range expected at the tap of potentiometer 156. Capacitors 168 and 169 effect conventional frequency compensation to the summing amplifier 148. The output from summing amplifier 148 is connected, through current limiting resistor 170, to one terminal of meter 150 which has its other terminal connected to ground potential. Back-to-back diodes 176, 177 are connected between the output of summing amplifier 148 and ground potential and serve to limit the voltage range applied to meter 150 to the forward potential of the diodes, thus protecting the sensitive movement of the meter.

Battery 141 (e.g. rechargeable 12 volt battery) provides power for circuitry 200 through converter/regulator 145 (e.g. +/−15 volt d-c/d-c convenerter/regulator) and regulator 146 (e.g. +/−5-volt d-c regulator) to properly control the voltages required. Battery 141 is preferably carried in an operator's shoulder strap rather than being stored within radiometer 10 to minimize the weight thereof, however it could be incorporated into the radiometer itself.

As set forth above, the output from summing amplifier 148 is fed to meter 150 (e.g. zero center voltage meter) which is mounted on panel 6 and is indicative of any instantaneous error due to a temperature change at filter 64. Those skilled in the art will understand that alternative null readout means, such as a green LED centered between two red LED's, can readily be substituted for the meter 150 through the use of suitable threshold detection circuitry.

To summarize the operation of circuitry 200, the signal input to summing amplifier 148, which drives the zero center meter 150, is electrically disposed as a tap-off of a resistive network situated between the temperature sensor 149 and an output (accessible at test point 178) from the LVDT intergrated circuit 147 which is indicative of the position of the LVDT body 125 with respect to the LVDT slug 124 (FIG. 3). If, during instrument calibration, the position of the LVDT slug 124 has been correctly set by the adjustment of rod 8 and the amplitude (span) output of the intergrated circuit 147 has been correctly set using potentiometer 165, an error signal will be present at the signal input to the summing amplifier which represents the error in the LVDT body 125 position (i.e., the position of the rod 109, which controls the angular position of the very narrow bandwidth filter 34, inasmuch as the rod 109 and LVDT body 125 are fixed together by the transducer mount 116) for the current temperature of the temperature sensor 149. The error may be quickly corrected by turning the micrometer head 7 to obtain a zero center reading of the meter 150, the correction being achieved without the necessity to refer to charts, read the micrometer head indicia, or perform any sort of mental and physical process beyond simply recentering the meter with the micrometer head 7. The correction can therefore easily be carried out as often as desired.

The accuracy of the periodic retuning of the very narrow bandwidth filter 64 to compensate for the effects of temperature change is subject to certain interrelated preliminary adjustments. More particularly, the angular translation of the filter mount 19 in response to manipulation of the micrometer head 7 must be accurately related to the error reading observed on the meter 150 if centering the meter is to satisfactorily effect the correction. It has been found, by way of example, that a typical filter 67 having a nominal center frequency of 5890 Angstroms and a diameter of two inches can be corrected through a range of 50 degrees Centigrade with a total axial translation of the rod 109 of approximately 0.1 inch. This corresponds to four turns of a typical micrometer head 7, and the tuning effect is linear over the temperature ranges which are expected during operation.

The principal adjustment to the temperature compensation subsystem is the gain potentiometer 165 of the integrated circuit 147, FIG. 11, which is the front panel "scalar" control identified as 18 in FIG. 2. The scalar control 18 (controls potentiometer 165) is a multiple turn unit (e.g. 25 turns) provided with an integral counter and indicia. Once the correct gain for integrated circuit 147 has been established (by finding the setting that gives correct tuning for the filter 64 for at least two different temperatures when the meter 150, is centered; i.e., nulled), the indicia of scalar 18 setting may be recorded for future use in conjunction with a particular optical filter assembly 16 in radiometer 10. When such future use is contemplated, it is only necessary to return the scalar 18 to the recorded indicia setting to reestablish tracking between the temperature compensation electronic subsystem and that particular optical filter tray assembly.

Figure 14:
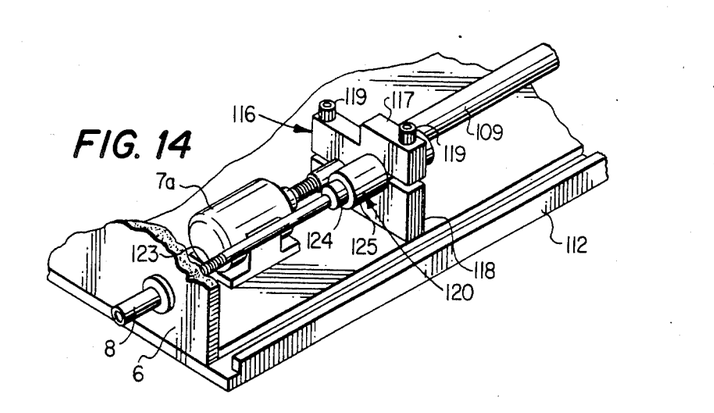
FIG. 14 is a further embodiment of FIG, 3.

Referring now to FIGS. 11 and 14, an embodiment of the present invention is shown where mount 19 is automatically adjusted in response to a change in temperature of filter 64. The error signal from circuitry 200 is fed to an electrically-driven motor 7a through lead 201 which rotates rod 109 and adjusts LDVT 120 to retune filter 64. When properly tuned, there will be no output signal from circuitry 200 so motor 7a will automatically stop.

Figure 15:
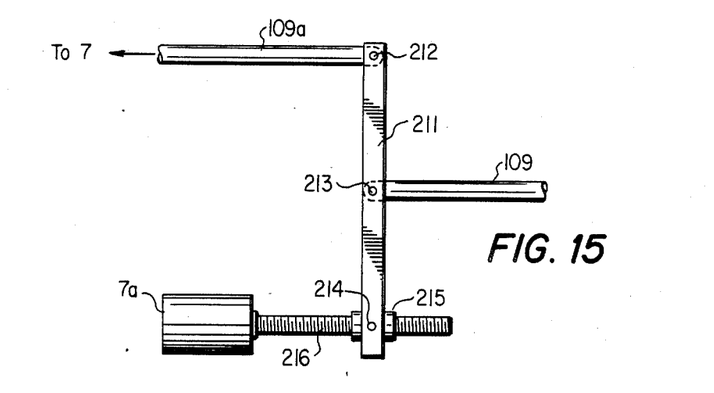
FIG. 15 is an elevation view of a still further embodiment of the present invention.

In FIG. 15, a mechanism 210 is disclosed which allows either manually retuning filter 64 by micrometer 7 or automatically by motor 7a, as desired. Mechanism 210 is comprised of bar 211 pivotably connected at one end 212 to rod 109a which, in turn, can be moved in or out by micrometer 7. Rod 109, which adjusts mount 19 as explained above, is pivotably connected to an intermediate point 213 on bar 211. Pivotably mounted in the other end 214 of bar 211, is nut 215 which is adapted to receive the treaded output shaft 216 of motor 7a.

If micrometer 7 is used to adjust filter 64, bar 21 will pivot about pivot 214 (nut 215) to move rod 109 in or out to rotate mount 19 as explained above. If adjustment is to be made automatically, bar 211 will pivot about pivot 212 as shaft 216 is rotated within nut 215 to thereby move rod 109.

What is claimed is:

1. A radiometer for detecting certain components of luminescense and reflected light energy contained in a light beam from a target wherein the reflected light includes a particular Fraunhofer line, said radiometer comprising:
a housing having an aperture therein for receiving said light from said target;
an optical filter assembly in said housing comprising:
a base plate;
a mount pivotably mounted on said base plate for rotation about an axis;
an optical passband filter mounted in said mount and positioned directly in the path of at least a fraction of said light beam, said filter having a center frequency substantially equal to the frequency of said particular Fraunhofer line, said filter being tunable to its said center frequency by angularly positioning said mount about its axis;
an adjustment rod in said housing having one end in contact with said mount whereby longitudinal movement of said rod changes the angular position of said mount about said axis;
means for sensing the longitudinal position of said adjustment rod and generating a first signal representative thereof.
a sensor means for sensing the temperature of said filter and generating a second signal representative thereof;
processing circuitry means comprising:
means for comparing said first and second signals and generating an error signal representative of the difference between said signals; and
means operably connected to the other end of said adjustment rod for longitudinally moving and adjusting said adjustment rod in response to said error signal to thereby retune said filter to its said center frequency when changes in temperature occur.

2. The radiometer of claim 1 wherein said means for adjusting said adjustment rod comprises:
a micrometer means on said housing operably connected to the other end of said adjustment rod whereby rotation of said micrometer means will longitudinally move said adjustment rod.

3. The radiometer of claim 1 wherein said means for adjusting said adjustment means comprises:
a motor means operably connected to the other end of said adjustment rod for longitudinally moving said adjustment rod.

4. The radiometer of claim 1 wherein said means for sensing the longitudinal position of said adjustment rod comprises:
a transducer comprising:
a body connected to said adjustment rod and movable therewith;
a slug slidably positioned in said body and fixed relative to said housing, and
means for sensing the position of said slug within said body and generating a signal representative thereof.

5. The radiometer of claim 4 wherein said means for adjusting said adjustment rod comprises:
a readout means for receiving said error signal and generating a visual readout thereof, said readout means also being responsive to the position of said adjustment rod; and
a micrometer means on said housing operably connected to the other end of said adjustment rod whereby rotation of said micrometer means will longitudinally move said adjustment rod.

6. The radiometer of claim 5 wherein said readout means comprises:
a zero center voltage meter.

7. The radiometer of claim 4 wherein said means for adjusting said adjustment rod comprises:
a motor means operably connected to the other end of said adjustment rod responsive to said error signal for longitudinally moving said adjustment rod.

* * * * *